(12) United States Patent
Blom et al.

(10) Patent No.: US 10,254,280 B2
(45) Date of Patent: Apr. 9, 2019

(54) CHANNEL FOR TRAPPING PARTICLES TO BE FED TO SAID CHANNEL WITH A FLUID

(71) Applicants: Micronit Microtechnologies B.V., Enschede (NL); Janssen Pharmaceutica NV, Beerse (BE); NXP B.V., Eindhoven (NL)

(72) Inventors: Marko Theodoor Blom, Enschede (NL); Monica Brivio, Enschede (NL); Simone Tanzi, Enschede (NL); Simon Reuvekamp, Enschede (NL); Bieke Van Dorst, Beerse (BE); Lieven Jozef Stuyver, Beerse (BE); Elfried Van Der Sar, Redhill (GB)

(73) Assignees: Micronit Microtechnologies B.V., Enschede (NL); Janssen Pharmaceutica NV, Beerse (BE); NXP B.V., Eindhoven (NL)

(*) Notice: Subject to any disclaimer, the term of this patent is extended or adjusted under 35 U.S.C. 154(b) by 68 days.

(21) Appl. No.: 15/233,427

(22) Filed: Aug. 10, 2016

(65) Prior Publication Data
US 2017/0045504 A1 Feb. 16, 2017

(30) Foreign Application Priority Data
Aug. 10, 2015 (NL) ...................................... 2015287

(51) Int. Cl.
*G01N 33/543* (2006.01)
*B01L 3/00* (2006.01)

(52) U.S. Cl.
CPC .... *G01N 33/54313* (2013.01); *B01L 3/50273* (2013.01); *B01L 3/502715* (2013.01);
(Continued)

(58) Field of Classification Search
CPC ........... B01L 3/502761; B01L 3/50273; B01L 3/502715; B01L 2200/0668;
(Continued)

(56) References Cited

U.S. PATENT DOCUMENTS

2010/0003666 A1 1/2010 Lee et al.
2011/0045994 A1 2/2011 Voldman et al.
(Continued)

FOREIGN PATENT DOCUMENTS

EP 2336781 A1 6/2011
WO WO-2012162779 A1 * 12/2012 ......... G01N 33/5005

OTHER PUBLICATIONS

Cho, Il-Hoon et al. "Lateral-flow enzyme immunoconcentration for rapid detection of Listeria monocytogenes." Anal. Bioanal. Chem. (2013) 405 3313-3319. (Year: 2013).*

*Primary Examiner* — Christopher Adam Hixson
(74) *Attorney, Agent, or Firm* — Rudy J. Ng; Bret E. Field; Bozicevic, Field & Francis LLP

(57) ABSTRACT

The invention relates to a channel for trapping particles to be fed to the channel with a fluid. The invention further relates to a flow cell comprising such a channel. The invention also relates to an assembly comprising such a flow cell and a detection means. The invention also relates to a method for trapping particles in such a channel. And finally, the invention relates to a method for analyzing a sample using such an assembly.

20 Claims, 9 Drawing Sheets

(52) U.S. Cl.
CPC .. *B01L 3/502761* (2013.01); *G01N 33/54386*
(2013.01); *B01L 2200/0668* (2013.01); *B01L
2300/0627* (2013.01); *B01L 2300/0816*
(2013.01); *B01L 2300/0851* (2013.01); *B01L
2300/0858* (2013.01); *B01L 2400/0406*
(2013.01); *B01L 2400/086* (2013.01)

(58) Field of Classification Search
CPC ..... B01L 2300/0627; B01L 2300/0858; B01L
2300/0816; B01L 2300/0851; B01L
2400/086; B01L 2400/0406; G01N
33/54313; G01N 33/54386
See application file for complete search history.

(56) References Cited

U.S. PATENT DOCUMENTS

2014/0127733 A1\* 5/2014 Altiok ............... B01L 3/502761
435/23
2014/0174933 A1 6/2014 Sudarsan et al.

\* cited by examiner

| ELISA type | Substrate | Lowest detectable mol conjugate |
|---|---|---|
| Chromogenic | pNPP | 0,1 pmol AP |
| Chromogenic | ABTS | 0,1 pmol HRP |
| Chromogenic | TMB | 1 fmol HRP |
| Fluorescent | β galactosidase resofurin | 3 amol β galactosidase |
| Chemiluminescent | Lumi Glo | 1 amol HRP |
| Chemiluminescent | PS atto | 1 amol HRP |
| Assembly according to the invention | PS atto | 0,1 amol HRP |

| Assay | Type | LLOD (pg/ml) |
|---|---|---|
| alphaLISA (PerkinElmer) | Amplified luminescent proximity assay | 300 |
| Innotest (Fujierbio) | | 65 |
| Life technologies | Colormetric | <10 |
| USCN Lifescience | Colormetric | 4,53 |
| IBL America | Colormetric | 4,03 |
| Sensolyte (Anaspec) | Colormetric | 2 |
| Assembly according to the invention | Chemiluminescent | 1 |

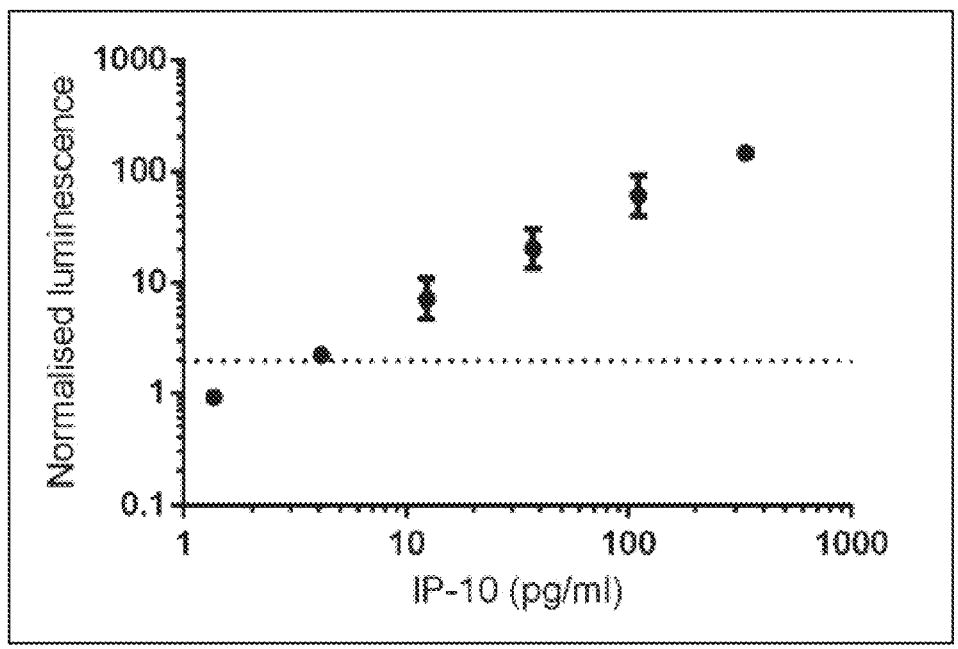

FIG. 6A

| Assay | Type | LLOD (pg/ml) |
|---|---|---|
| Luminex human IP10-kit (Biosource/Invitrogen) | Fluorescent bead based | 5 |
| ELISA DuoSet (R&D systems) | Colorimetric | 5 |
| ELISA OptEIA (BD biosystems) | Colorimetric | 5 |
| Assembly according to the invention | Chemiluminescent | 4 |
| Luminex Lincoplex (Linco research) | Fluorescent bead based | 3,1 |
| Novex human IP10 ELISA kit (Life technologies) | Colorimetric | 2 |
| IP-10 (CXCL10) Human in vitro SimpleStep ELISA (Abcam) | Colorimetric | 1,4 |

FIG. 6B

CHANNEL FOR TRAPPING PARTICLES TO BE FED TO SAID CHANNEL WITH A FLUID

CROSS-REFERENCE TO RELATED APPLICATION

This application claims priority to the filing date of Netherlands application serial no. NL2015287, filed Aug. 10, 2015; the disclosure of which application is herein incorporated by reference.

INTRODUCTION

Field of the Invention

The invention relates to a channel for trapping particles to be fed to the channel with a fluid, said channel having a bottom and opposite sidewalls, the sidewalls defining a width of the channel. The invention further relates to a flow cell comprising such a channel. The invention also relates to an assembly comprising such a flow cell and a detection means. The invention also relates to a method for trapping particles in a channel. The invention also relates to a method for analyzing a sample using such an assembly.

Background

Channels for trapping particles are known per se and may for example be part of a microfluidic detection module or analysis system. Usually, in such systems functionalized micro beads are fed to the channel with a fluid and trapped in a particle trapping area thereof. A sample with target molecules is then fed to said channel, wherein said micro beads are arranged to capture said target molecules from said sample. Alternatively, the beads may be coated with the target molecules prior to feeding the particles to the channel. The particle trapping area is arranged in the vicinity of a sensor, such that the captured target molecules may be sensed thereby.

Prior art document US 2010/003666 A1 discloses a method for detection of molecular recognition and analysis of cells. The method makes use of a specific microfluidic system architecture for conducting biomolecular and cell assays. This architecture includes an array of U-shaped weir-traps, which are arranged in a flow chamber which is formed between a substrate and a cover. Each weir-trap is shaped as a rectangular block having a semi-circular recess in its upstream face. Each weir-trap has a height that is less than the distance between the substrate and the cover, so that a reduced fluid flow space is formed, which is smaller than the size of particles entrained in the fluid flow through the device. The weir-traps are arranged in parallel rows perpendicular to the inflow direction, and weir-traps in each row are offset with respect to weir-traps in an adjacent row. The particles in this document are biological agents, e.g. a cell or an analyte. Analysis instrumentation may be associated with each individual weir-trap or with the trapping array as a whole.

Prior art document US 2014/174933 A1 discloses a droplet actuator comprising a base substrate on which rows of electrodes are arranged for performing droplet operations, e.g. to transport a droplet. Droplets may comprise one or more beads, which may carry targets of interest. In the embodiment of FIG. 3 of this document a U-shaped barrier is arranged over a row of electrodes to restrain transport of beads in the droplets. The droplets are immersed in a filler fluid with which they do not mix. The filler fluid and droplets are held in a space between a lower substrate carrying the electrodes and an upper substrate associated with a ground electrode 138. The barrier is suspended from the upper substrate and has a height which is smaller than the distance between the upper and lower substrate, thus leaving free a distance through which the droplet may flow. Beads will be restrained by the barrier. Although the beads are said to carry targets of interest, this document does not disclose any detection means.

In prior art document US 2011/045994 A1 a device and method are disclosed for microscale particle capturing and particle pairing, i.a. for high yield assaying. The device includes a particle patterning device having an array of capture units. The capture units are arranged in rows or columns, with capture units in one row offset from units in an adjacent row. Each capture unit has a first and second chambers or capture cups on opposite sides. The first chamber serves to capture the first particle, which is then transferred to a second chamber of an opposing capture unit by reversal of flow. Then a second particle is captured in the second chamber and the first and second particles bind or react. Due to the presence of chambers on opposite sides each capture unit is H-shaped, rather then U-shaped. The device further includes a light source and a detector mounted opposite the light source for visual detection of the trapped particles.

And finally, prior art document EP 2 336 781 A1 discloses a cell and a method for testing or analyzing disk-shaped microbeads. These microbeads are covered with a probe substrate that has affinity for a target substrate. The test cell includes a containing space that is closed off by a sealing pillar. The containing space is partitioned by a partition pillar into a supply space having a supply port and a discharge space having a discharge port. The partition pillar is made up of pillar members and spaces or cut outs there between. The microbeads supplied from the supply port are collected or concentrated in a Ω-shaped part of the partition pillar. The containing space is arranged between a support substrate and a transparent cover, and an image detector is provided for analyzing samples.

SUMMARY

It is an object of the invention to provide an improved channel for trapping particles. In particular it may be an object of the invention to provide a channel for trapping particles with an increased filling speed.

This object is achieved by providing a channel according to the preamble, which channel comprises:
 a first channel part;
 a second channel part in fluid through flow connection with said first channel part and downstream of said first channel part;
 an elevated structure provided in said channel that divides said channel in said first channel part and said second channel part and for trapping particles in said first channel part;
 at least one flow gap provided by said elevated structure for providing said fluid through flow connection between the first channel part and the second channel part for allowing, in use, at least some fluid to flow past said elevated structure into said second channel part while trapping said particles in said first channel part;
 wherein said elevated structure is substantially U-shaped and has a base extending substantially between the opposite sidewalls of the channel and two legs extending from the base in an upstream direction, wherein at least part of said U-shaped elevated structure defines at least part of a particle trapping area for trapping the particles to be fed to said channel.

Filing of the particle trapping area of said channel with particles occurs by feeding a fluid with particles to said first channel part. The at least one flow gap provided by said elevated structure has at least one of a width or a height that is smaller than a smallest dimension of said particles, such that the particles cannot flow there through and will be trapped in the first channel part in said particle trapping area, while at least some of the fluid will flow through said flow gap past said elevated structure into said second channel part. An advantage of the elevated structure being substantially U-shaped is that the flow resistance offered by the particles trapped in the particle trapping area and the elevated structure is relatively low, such that filling of the particle trapping area may occur relatively fast.

Such a substantially U-shaped elevated structure extending substantially between the sidewalls of the channel in particular provides the advantage of providing a relatively large flow gap area for passing of liquid and a relatively large area for trapping particles for a relatively small width of the channel. This is because the elevated structure and thereby the at least one flow gap is not only provided over the width of the channel but also over a part of the length of the channel at two longitudinal sides thereof. In particular the base of the U-shaped elevated structure and thereby the at least one flow gap provided by the base extends substantially orthogonal to the longitudinal direction of the channel and thus over the width of the channel, or at least the width of the first channel part. The legs of the U-shaped elevated structure and thereby the at least one flow gap provided by the legs extend substantially parallel to the longitudinal direction of the channel and thus over said part of the length of the channel at the two longitudinal sides thereof.

The flow gap, or plurality of flow gaps together, hereby also define a substantially U-shaped shape having a base and two legs extending from the base in an upstream direction.

It is noted that said particles to be fed to said channel may be any suitable particles. For example, said particles may be substantially spherical beads. In such a case the width and height of the flow gap are chosen such that at least one thereof is smaller than the diameter of the beads.

It is further noted that the fluid to be fed to said channel may be any suitable fluid, either a gas or a liquid. For example, said fluid may be chosen from the group consisting of inert gasses and aqueous solutions.

Said flow gap may be provided in any suitable way.

For example said flow gap may comprise a plurality of substantially vertical gaps in the elevated structure.

In another embodiment of the channel according to the invention said flow gap is provided by at least a part of said elevated structure having a height that is smaller than at least a local height of said channel in the area of the elevated structure.

This way, the fluid may flow over the elevated structure in the second channel part, while trapping the particles in the first channel part.

Said part, or parts, of said elevated structure having a height that is smaller than at least a local height of said channel in the area of the elevated structure preferably extends over at least part of the base and at least part of each leg of the U-shaped elevated structure.

In an embodiment of the channel according to the invention the flow gap defined by said elevated structure having a height that is smaller than at least a local height of said channel in the area of the elevated structure may be provided over substantially the whole length of the U-shaped elevated structure.

Said flow gap may be substantially one continuous flow gap, optionally disrupted with spacer elements, as described below.

Said channel may be covered by a cover, for example a substrate. In such an embodiment the local height of said channel is defined between the local bottom of the channel and the local (lower) side of the cover facing the channel.

Optionally at least one spacer element is provided for spacing said cover from said bottom and/or from said elevated structure, thereby maintaining said gap provided between the elevated structure and the cover. For example, a plurality of spacer elements, each having the form of a cylindrical or beamlike pillar may be provided, that extend between the elevated structure and the cover or between the bottom of the channel and the cover.

The gap defined by said elevated structure having a height that is smaller than at least a local height of said channel in the area of the elevated structure is chosen to be smaller than the smallest dimension of the particles, thereby preventing the particles from flowing there through. For example, but not limited thereto, said particles may have a smallest dimension of between 2-4 µm, while said gap may have a height of less than 2 µm, for example between 1.0-1.9 µm.

The height of said gap may be constant or vary over the length of the elevated structure.

In another embodiment of the channel according to the invention said legs have a substantially uniform width over the lengths thereof.

An advantage of this embodiment is that the fluidic resistance of the fluid flowing through the flow gap is substantially uniform over the length of the legs.

In another embodiment of the channel according to the invention said legs have a substantially tapering width in a downstream direction.

An advantage of this embodiment is that the fluidic resistance of the fluid flowing through the flow gap depends on the local width of the legs, wherein an increased width results in a higher fluidic resistance and vice versa.

If the width of the legs tapers from relatively wide to relatively narrow in said downstream direction of the channel, the fluidic resistance of the flow gap of the legs decreases towards the base of the elevated structure, such that in the beginning of the trapping process, the particles tend to be trapped near the base of the elevated structure. This provides a more even filling of the particles, as filling starts from the base towards the free ends of the legs, and thereby reduces the risk on obtaining unfilled areas closed off by surrounding particles.

In another embodiment of the channel according to the invention said legs have a length that is between 0.5 to 1 times the length of the particle trapping area.

The particle trapping area may thus be just as long as the legs of the elevated structure up to twice as long as the legs of the elevated structure, such that the particle trapping area is also defined by part of the longitudinal side walls of the first channel part.

In another embodiment of the channel according to the invention said second channel part is at least locally wider than said first channel part in the area of the elevated structure.

Said locally wider second channel part, which may surround the U-shaped elevated structure, allows the fluid to flow through the flow gap under an angle to the main flow direction as defined by the longitudinal axis of the channel. This in turn allows allows the fluid to flow through the flow gap in the second channel part over substantially the whole length of the U-shaped elevated structure.

In another embodiment of the channel according to the invention said channel has a relatively large width compared to its height.

Such a channel provides a particle trapping area that has a relatively large surface area compared to its height. This may for example allow a good sensing of captured target molecules.

For example, but not limited thereto, the channel may be between 300-1000 µm wide, and may have a height between 6-12 µm.

In an embodiment of the channel according to the invention the width of the channel may be more than 25 times its height, preferably more than 75 times its height, and most preferably more than 125 times its height.

In another embodiment of the channel according to the invention said channel is a microfluidic channel.

In another embodiment of the channel according to the invention said channel has capillary action.

The invention further relates to a flow cell, said flow cell comprising:
 a channel according to any of the embodiments described above or any combination thereof, and
 an inlet port and an outlet port that are in fluid through flow connection with said channel.

Said inlet port may be in fluid through flow connection with said first channel part and may be used for feeding said fluid with particles to said first channel part. Said outlet port may be in fluid through flow connection with said second channel part and may be used for discharging said fluid from said second fluid part.

The invention further relates to an assembly of a flow cell according to any of the above described embodiments or combination thereof and a detection means.

Said detection means may be used for detecting target molecules of a sample to be analyzed.

Said detection means may for example comprise a microscope or a sensor. Said sensor may for example be an optical sensor, such as a luminescent, fluorescent, or optical density sensor, or an electronical sensor, such as a conductimetric, amperometric, or potentiometric sensor.

Said detection means and flow cell may either be connected to each other, either in a fixed manner or releasably, or may not be connected to each other. The assembly of the detection means and flow cell may optionally be provided in a common package, even if they are not connected to each other.

In a preferred embodiment, the assembly comprises the detection means as an integrated element. The advantage of having the detection means as an integrated element is that the assembly may be used as a point-of-care test without the need for external readout instruments. The assembly can thus be used in a mobile or peripheral setting, such as for instance at the patient's bedside or in resource limited countries with limited access to hospitals and clinical labs.

The assembly comprising the flow cell according to any of the above described embodiments or combination thereof and a detection means can be used for the analysis of samples. Molecules in such samples can be measured with high sensitivity due to the design of the channel according to the invention. With high sensitivity is meant a sensitivity comparable to or higher than the sensitivity achieved with classical lab-based assays, and a sensitivity higher than the classical point-of-care tests currently used, such as for instance lateral flow tests, dipstick tests, etc.

The invention further relates to a method for trapping particles in a channel, optionally of a flow cell, said method comprising the steps of:

(a) providing a said channel according to any of the above described embodiments or combination thereof or a flow cell according to any of the above described embodiments or combination thereof;

(b) feeding a fluid with particles to be trapped to said first channel part for trapping said particles in said particle trapping area.

Prior to feeding the particles to the channel in step (b), said particles may be coated with target molecules and/or capture molecules.

Capture molecules are molecules that bind target molecules through a specific interaction. Target molecules are molecules that are to be measured, and will bind to the capture molecules when these are brought into contact with each other. Capture molecules can thus be used as a means in the measurement of target molecules. Said target molecules may be target molecules of a sample to be analyzed, such as for example peptides or proteins, including but not limited to disease specific biomarkers, antibodies or small molecules in clinical samples, and/or chemical agents in clinical, environmental and/or food samples. Said capture molecules may for example be DNA, peptides and/or proteins, such as for instance antibodies, antigens, receptors, ligands, etc. Said capture molecules may be arranged to capture target molecules of a sample to be analyzed to allow for their specific interaction with the target molecule, In another embodiment of the method according to the invention the particles that are fed to said first channel part in step (b) have a smallest cross sectional size that is larger than said at least one flow gap, thereby preventing said particles from flowing through said flow gap.

The invention further relates to a method for analyzing a sample, said method comprising the steps of:

(a) providing an assembly according to any of the above described embodiments or combination thereof;

(b) feeding a fluid with particles to be trapped to said first channel part for trapping said particles in said particle trapping area, said particles being coated with capture molecules for capturing target molecules from said sample to be analyzed;

(c) feeding said sample to be analyzed to said first channel part, and (d) analyzing said sample by means of said detection means.

With "analyzing" is meant the detection of the presence of target molecules and the quantity thereof.

The presence of target molecules, i.e. whether the capture molecules on the particles have bound any target molecules in the sample to be analyzed, can be detected in various ways known to the skilled person. This may, for instance, be achieved by labeling a detection molecule with a fluorescent, chemiluminescent, or radioactive label, and feeding the labelled detection molecule to the particles and sample to be analyzed in said first channel part. This may also be achieved by means of an enzymatic reaction.

Accordingly, in a preferred embodiment the method comprises the steps of:

(a) providing an assembly according to any of the above described embodiments or combination thereof;

(b) feeding a fluid with particles to be trapped to said first channel part for trapping said particles in said particle trapping area, said particles being coated with capture molecules for capturing target molecules from said sample to be analyzed;

(c) feeding said sample to be analyzed to said first channel part, (d) feeding a detection antibody conjugated to an enzyme to said first channel part,
(e) feeding a substrate which reacts with the enzyme conjugated to the detection antibody to said first channel part; and
(f) analyzing said sample by means of said detection means.

The invention further relates to a method for analyzing a sample, said method comprising the steps of:
(a) providing an assembly according to any of the above described embodiments or combination thereof;
(b) feeding a fluid with particles to be trapped to said first channel part for trapping said particles in said particle trapping area, said particles being coated with target molecules of a sample to be analyzed;
(c) analyzing said sample by means of said detection means.

With "analyzing" is meant the detection of the presence of target molecules and the quantity thereof.

The presence of target molecules can be detected in various ways known to the skilled person. This may, for instance, be achieved by labeling a detection molecule with a fluorescent, chemiluminescent, or radioactive label, and feeding the labelled detection molecule to the particles coated with the target molecules in said first channel part. This may also be achieved by means of an enzymatic reaction. Accordingly, in a preferred embodiment the method comprises the steps of:
(a) providing an assembly according to any of the above described embodiments or combination thereof;
(b) feeding a fluid with particles to be trapped to said first channel part for trapping said particles in said particle trapping area, said particles being coated with target molecules of a sample to be analyzed;
(c) feeding a detection antibody conjugated to an enzyme to said first channel part,
(d) feeding a substrate which reacts with the enzyme conjugated to the detection antibody to said first channel part; and
(e) analyzing said sample by means of said detection means.

BRIEF DESCRIPTION OF THE FIGURES

The invention will be further elucidated with reference to figures shown in a drawing:

FIG. 6A: Detection of IP-10 by a chemiluminescent bead ELISA with readout in the assembly comprising the flow cell according to the invention and an optical CMOS sensor. The error bar shows the SD of the triplicate measurements and the dotted line shows the threshold value, defined by "The average of the blank+3×SD" (n=3).

FIG. 6B: Table showing the performance of chemiluminescent bead ELISA with readout in the assembly comprising the flow cell according to the invention and an optical CMOS sensor compared with commercial available IP-10 lab-based assays, according to LLOD reported by manufacturers.

FIG. 1A shows a flow cell 1. Said flow cell 1 comprises a first substantially planar substrate 2, comprising two substrate layers 2A, 2B that are bonded to each other. The substrate layers 2A, 2B can be made from any suitable material, for example glass, silicon or ceramic. In a first substrate layer 2A of said first substrate 2, a channel comprising a first channel part 3 and a second channel part 4 is provided, for example by means of etching. Said channel is sealed by the second substrate layer 2B that is provided on top of the first substrate layer 2A. Said second channel part 4 is in fluid through flow connection with said first channel part 3 and is located downstream of said first channel part 3. An inlet reservoir 5 connects to the first channel part 3 for feeding a fluid thereto. An outlet reservoir 6 connects to the second channel part 3 for discharging a fluid therefrom.

DETAILED DESCRIPTION

Figure 1A:
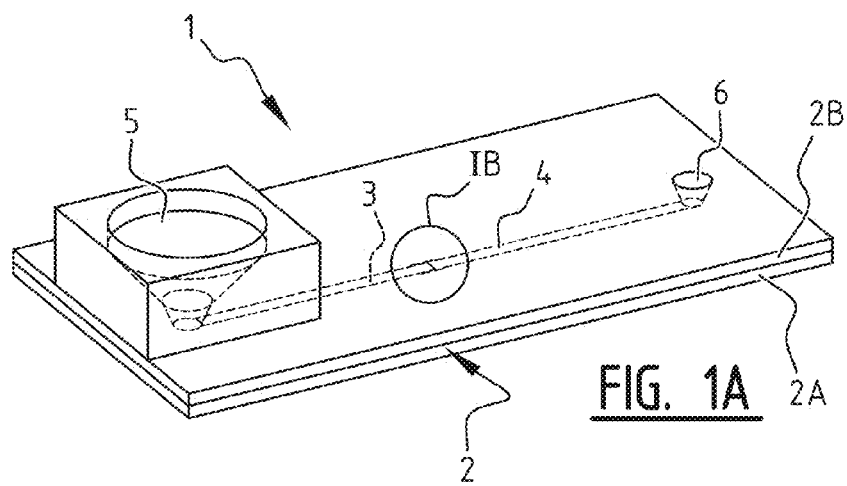
FIG. 1A: A schematic perspective view of a part of a flow cell according to an embodiment of the invention.

Before the present invention is described in greater detail, it is to be understood that this invention is not limited to particular embodiments described, as such may, of course, vary. The invention encompasses various alternatives, modifications, and equivalents, as will be appreciated by those of skill in the art. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is noted that, as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order which is logically possible.

Any publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention.

Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Figure 1B:
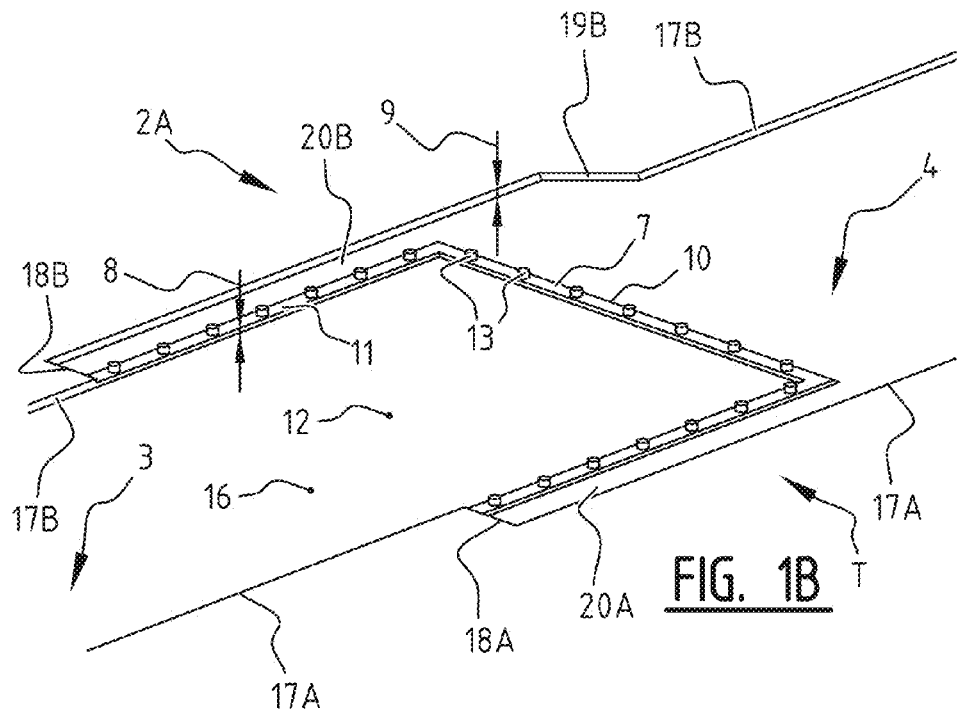
FIGS. 1B and 1C: A detailed view of a particle trapping area of the flow cell of FIG. 1A.
Figure 1C:
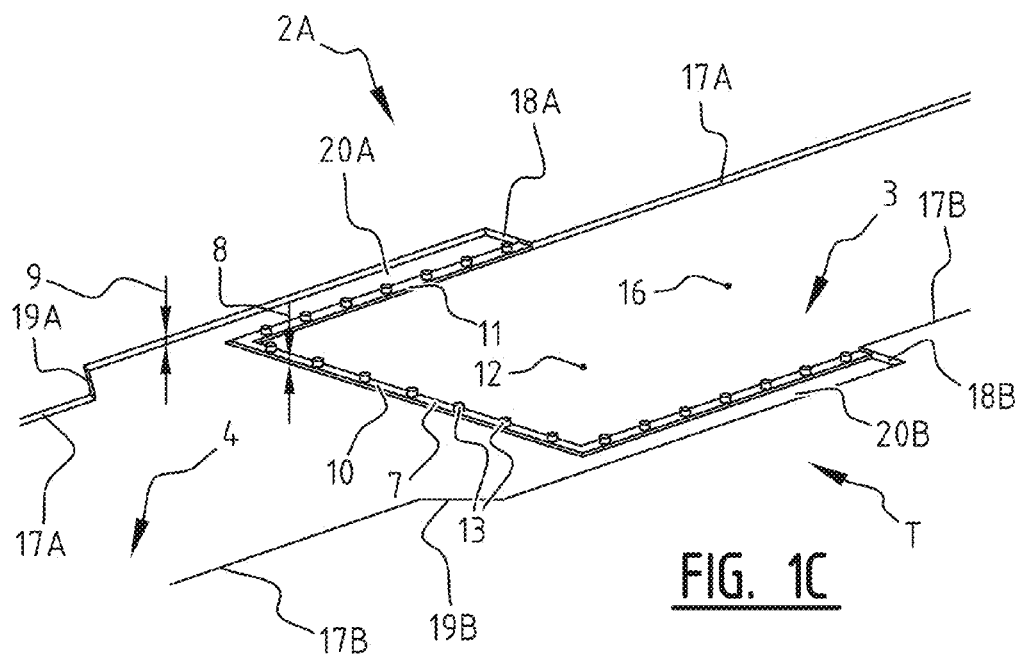

FIGS. 1B and 1C show a transition area T of the first channel part 3 to the second channel part 4. FIG. 1B shows the transition area T in a downstream view and FIG. 1C shows the transition area T in an upstream view. These figures show that each channel part 3, 4 has a bottom 16 and is bounded by opposite sidewalls 17A, 17B. These figures further show how an elevated structure 7 provided in the channel divides said channel in said first channel part 3 and said second channel part 4. In the illustrated embodiment the elevated structure 7 has a height 8 that is smaller than at least a local height 9 of said channel in the area of the elevated structure 7, thereby providing a flow gap between the elevated structure 7 and the second substrate layer 2B provided on top of the channel. The height of the flow gap is smaller than the diameter of the beads or particles 14 which are carried along by the fluid in the first channel part 3. Said flow gap provides said fluid through flow connection between the first channel part 3 and the second channel part 4 for allowing at least some fluid to flow past said elevated structure 7 into said second channel part 4 while trapping particles to be fed to said first channel part 3 with said fluid in said first channel part 3.

In the illustrated embodiment the elevated structure 7 functions as a weir, defining a horizontal flow gap between its top and the top of the channel (or lower surface of the second substrate layer 2B). However, it is also conceivable that one or more vertical flow gaps are defined by the elevated structure. This could be done by forming the elevated structure from a plurality of closely spaced pillars or wall parts extending from the bottom to the top of the channel. In that case the spacing between adjacent pillars or wall parts should be smaller than the diameter of the beads or particles 14.

The elevated structure has a substantially U-shaped shape having a base 10 and two legs 11 extending from the base in an upstream direction, i.e. in the direction of the inlet reservoir 5. The second channel part 4 is locally wider than said first channel part 3 over a length of the channel in the vicinity of, and in particular starting from, the legs 11 up to beyond the base 10 of the elevated structure. In the illustrated embodiment two outwardly extending perpendicular wall parts 18A, 18B are arranged at the upstream ends of the legs 11, while two converging, inwardly angled wall parts 19A, 19B are formed downstream of the base 10, thus defining two sideflow areas 20A, 20B. This allows fluid to flow through said flow gap provided by the legs 11 into said second channel part 4, i.e. to flow under an angle with respect to the main fluid flow direction as defined by the longitudinal axis of the channel. The base 10 and the legs 11 together define part of a particle trapping area 12 for trapping particles, as will be described in further detail with respect to FIGS. 3A and 3B. Spacer elements in the form of substantially cylindrical pillars 13 are provided on top of the elevated structure 7 for maintaining the second substrate layer in its position spaced apart from said elevated structure 7, thereby maintaining the flow gap. Said U-shaped elevated structure provides substantially one continuous U-shaped flow gap, that is only disrupted by said pillars 13.

Figure 2A:
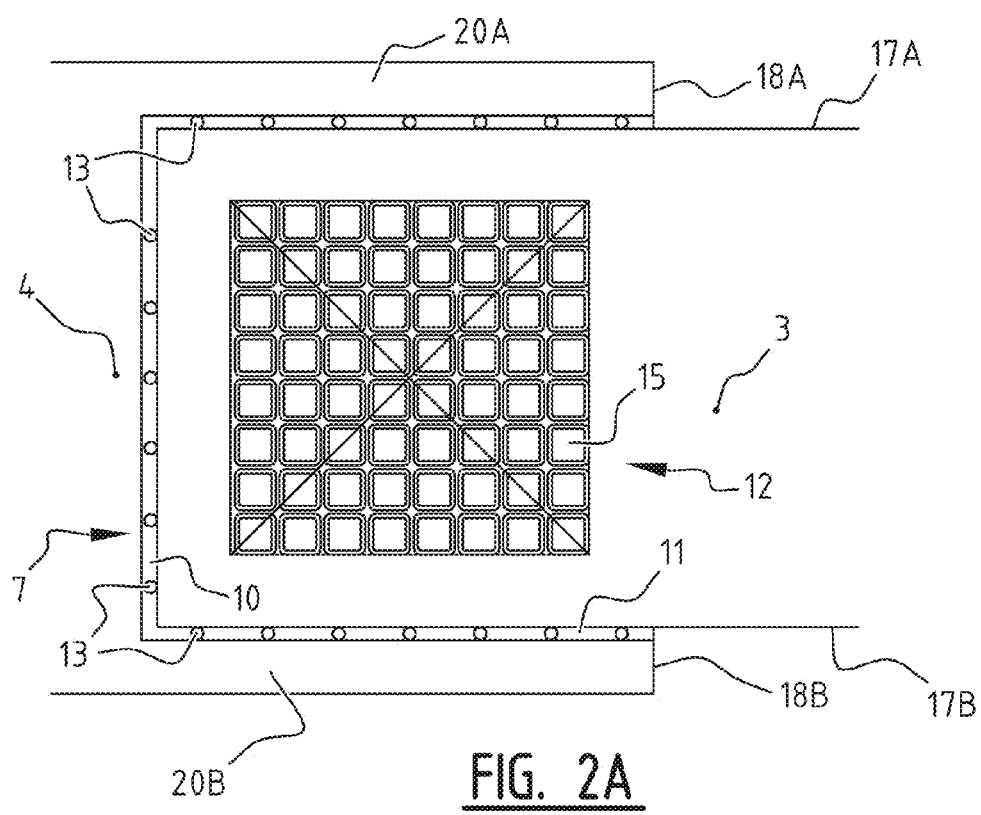
FIGS. 2A and 2B: A schematic top view of two embodiments of the elevated structure according to the invention.
Figure 2B:
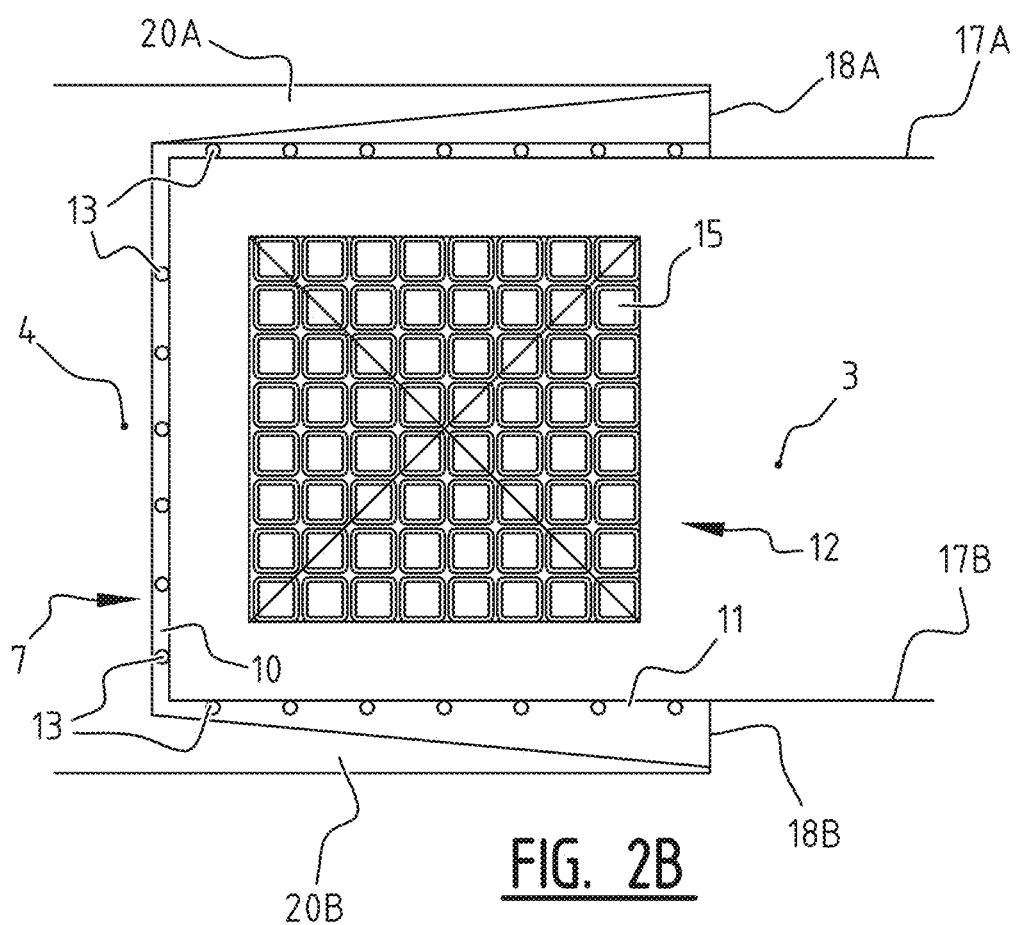

FIGS. 2A and 2B each show an embodiment of the elevated structure 7 according to the invention.

In FIG. 2A the legs 11 have a substantially uniform width over the lengths thereof. An advantage of this embodiment is that the fluidic resistance of the fluid flowing through the flow gap is substantially uniform over the length of the legs 11.

In FIG. 2B the legs 11 have a substantially tapering width in a downstream direction, i.e. the width of the legs reduces in the downstream direction. The downstream direction is defined in the direction of the outlet reservoir 6. An advantage of the tapering width is that the fluidic resistance of the flow gap of the legs 11 decreases towards the base 10 of the elevated structure 7, such that in the beginning of the trapping process, the particles 14 tend to be trapped near the base 10 of the elevated structure 7. This provides a more even filling of the particles, as filling starts from the base 10 towards the upstream ends of the legs 11.

As is further shown in FIGS. 2A and 2B, part of said particle trapping area 12 is located in the vicinity of a sensor for providing a sensor area 15. The particles trapped in the sensor area 15, and in particular any target molecules captured thereby or coated thereon, may be sensed with use of any suitable sensor.

It is noted, that the elevated structure is not limited to the embodiments shown in FIGS. 2A and 2B, but may have any suitable substantially U-shaped shape.

For example, the base 10 may optionally be substantially curved instead of straight, as seen from above.

For example, the legs 11 may have a substantially tapering width in an upstream direction, i.e. the width of the legs reduces in the upstream direction.

For example, the legs 11 may have any varying width over the lengths thereof, thereby providing a varying fluidic resistance over the lengths of the legs 11.

Figure 3A:
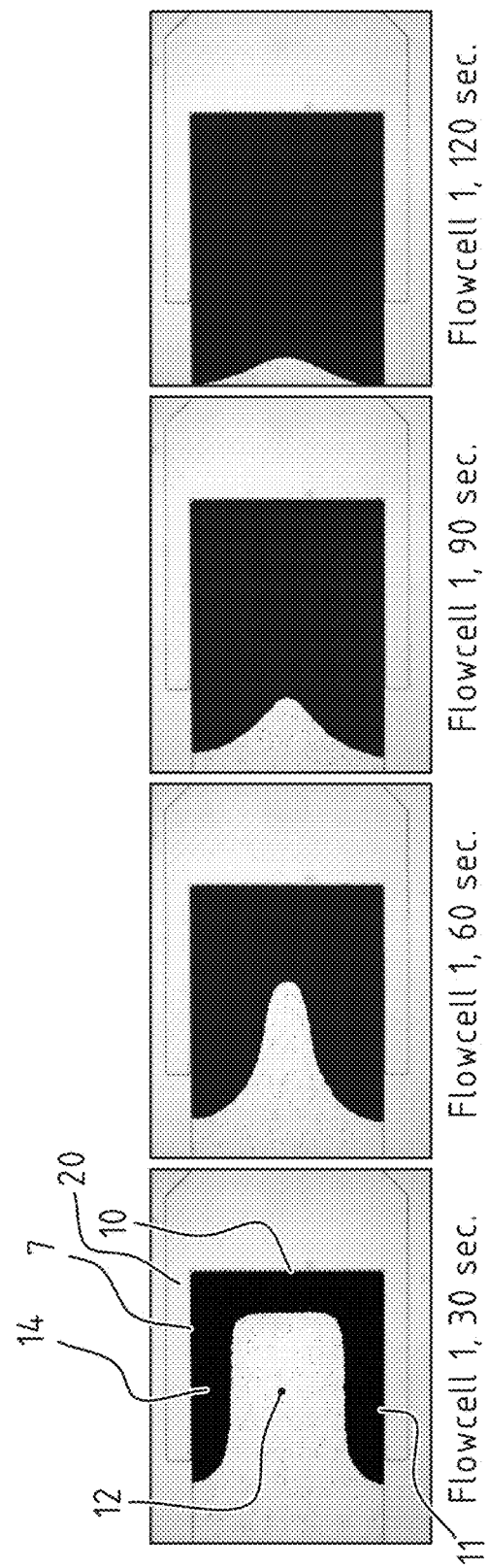
FIG. 3A: Photo's showing the filling of the particle trapping area of the embodiment of FIG. 2A.

FIG. 3A shows the filling of the particle trapping area 12 of a channel having the elevated structure 7 of FIG. 2A at time frames of 30 second, 60 seconds, 90 seconds and 120 seconds. The particles are denoted by reference numeral 14.

Figure 3B:
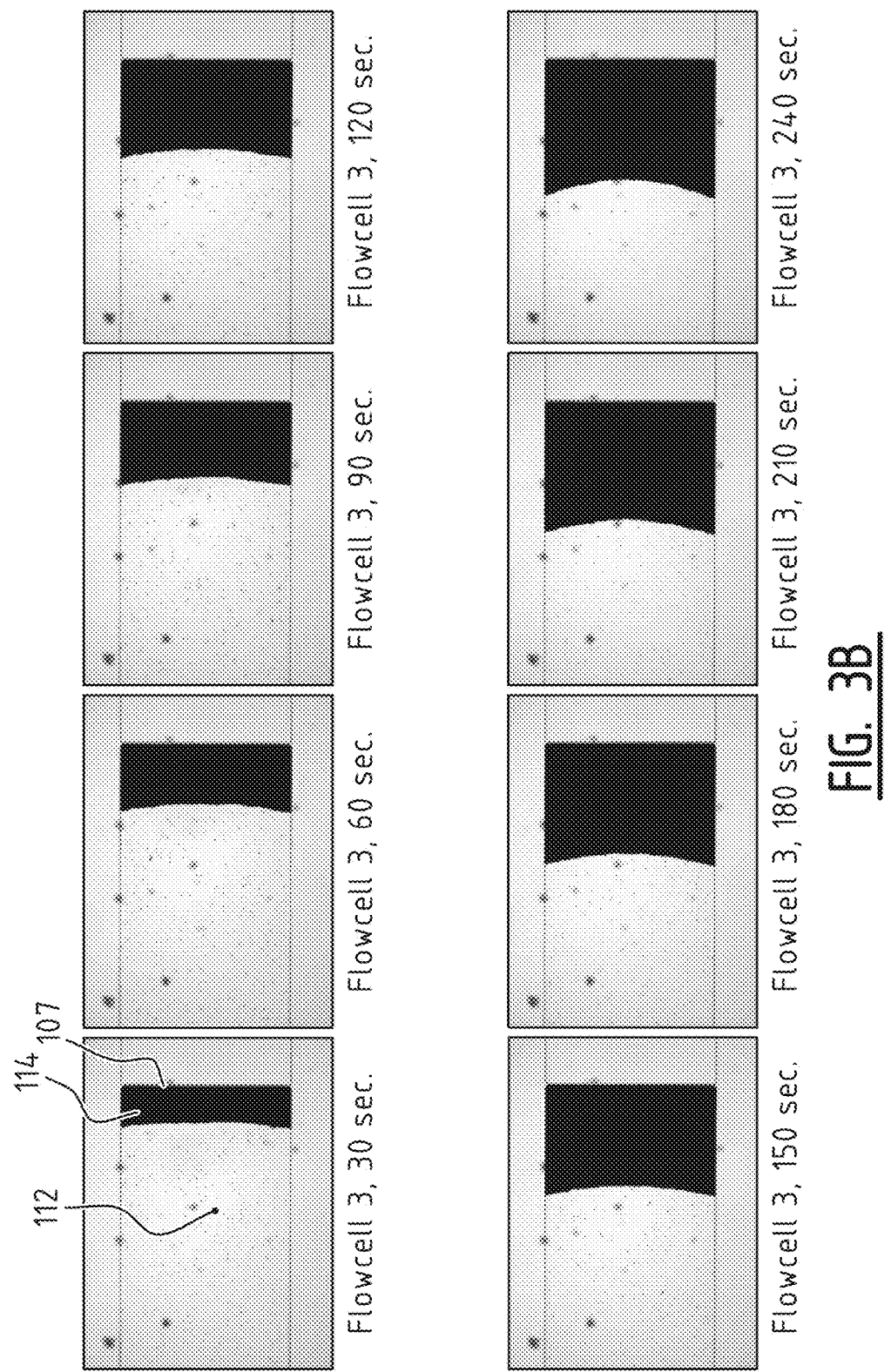
FIG. 3B: Photo's showing the filling of the particle trapping area of an elevated structure that is not part of the invention.

FIG. 3B shows the filling of the particle trapping area of a channel that is not part of the invention. In FIG. 3B the same reference numerals are used for denoting the same elements, but increased by 100. The channel of FIG. 3B has similar dimensions as the channel of FIGS. 2A and 3A. In particular the first and second channel parts of FIG. 3B have substantially the same width as the first channel part of the channel of FIGS. 2A and 2B. The channel of FIG. 2B has a one sided elevated structure 70 that extends orthogonal to the longitudinal direction. The particle trapping area 112 is defined by part of the first channel upstream of the elevated structure 70. Filling of the particle trapping area 112 with particles 114 is shown at time frames of 30 second, 60 seconds, 90 seconds, 120 seconds, 150 seconds, 180 seconds, 210 seconds and 240 seconds.

FIGS. 3A and 3B show that the speed of filling of the particle trapping area 12 of the channel according to the invention as shown in FIG. 3A is relatively high with respect to the channel of FIG. 3B. In particular, the particle trapping area 12 of the channel according to the invention as shown in FIGS. 2A and 3A, is substantially filled after 120 seconds, while the particle trapping area 112 of the channel of FIG. 3B is not even completely filled after 240 seconds. The filling speed of the channel of FIG. 3B significantly reduces with an increasing number of particles trapped in the particle trapping area 112, due to an increased flow resistance. The filling speed of the particle trapping area 12 of the channel according to the invention maintains relatively high. This is a result of the total flow resistance offered by the particles trapped in the particle trapping area 12 and the elevated structure 7 being relatively low.

It is noted that the invention is not limited to the shown embodiments but also extends to variants within the scope of the appended claims.

EXPERIMENTAL

Example 1

Protocol for Use of an Assembly Comprising the Flow Cell According to the Invention and an Optical CMOS Sensor in Sample Analysis An assembly comprising the flow cell according to the present invention and an optical CMOS sensor can be used for the analysis of fluid samples, such as for instance bodily fluids. The following protocol was used for the measurement of the samples prepared as described in Examples 2-5.

For each sample that was tested a different flow cell was used. To prepare the flow cells for detection, the flow cells were first connected with the demonstrator box and calibrated. After the calibration, the dark count (Average of n=10) was measured and the flow cells were primed from the outlet with PS-atto substrate (Lumigen) by the use of a 2 ml syringe.

The beads with target captured were dissolved in 10 μl of PS-atto substrate (Lumigen) and immediately added to the inlet reservoir of the flow cell. By applying vacuum at the outlet, the beads are loaded in the flow cell above the sensor area. After 6 min, the flow was stopped by taking off the vacuum from the outlet. The normalized luminescence at the moment the flow is stopped was used as readout signal. To be able to compare luminescent signals measured at different SPADs (single photon avalanche diodes), the normalized luminescence is calculated with the equation: Normalized Luminescence=(CPS−DC)/DC; With: CPS=The average counts per second of the active SPADs; DC=dark count (average of n=10).

Example 2

HRP IgG Detection with a Chemiluminescent Bead ELISA

In this assay, magnetic beads coated with Protein A were used to detect IgG conjugated with HRP (HRP-IgG) (Ortho Clinical Diagnostics, USA). For this assay, 5 mg of Dynabeads M-270 Epoxy (Life technologies, Gent, Belgium) were coated with 50 μg protein A (Thermoscientific, Leuven, Belgium) according to the manufacturer's instructions of the Dynabeads antibody coupling kit (Life technologies, Gent, Belgium). Before using the protein A coated beads for the detection of HRP-IgG, the beads were blocked with casein, by incubation in 1% casein PBS Buffer (Thermoscientific, Leuven, Belgium) on a roller at room temperature for 5 min (1 μl of 10 mg beads/ml in 99 μl blocking solution per sample). Afterwards, the beads were separated from the blocking solution with the use of an external magnet and 100 μl of HRP-IgG diluted in 1% casein PBS Buffer was added to the beads. The HRP-IgG was incubated for 30 min with the beads on a roller at room temperature. After this incubation, non-bound IgG were washed away in three wash steps with 200 μl PBST (PBS+0.05% Tween) and one wash step with 50 μl PBS. For each wash step, beads were separated from the liquid with the use of an external magnet and were dissolved in wash buffer. After the last wash step the detection was performed following the protocol as described in Example 1.

Figures 4A, 4B:
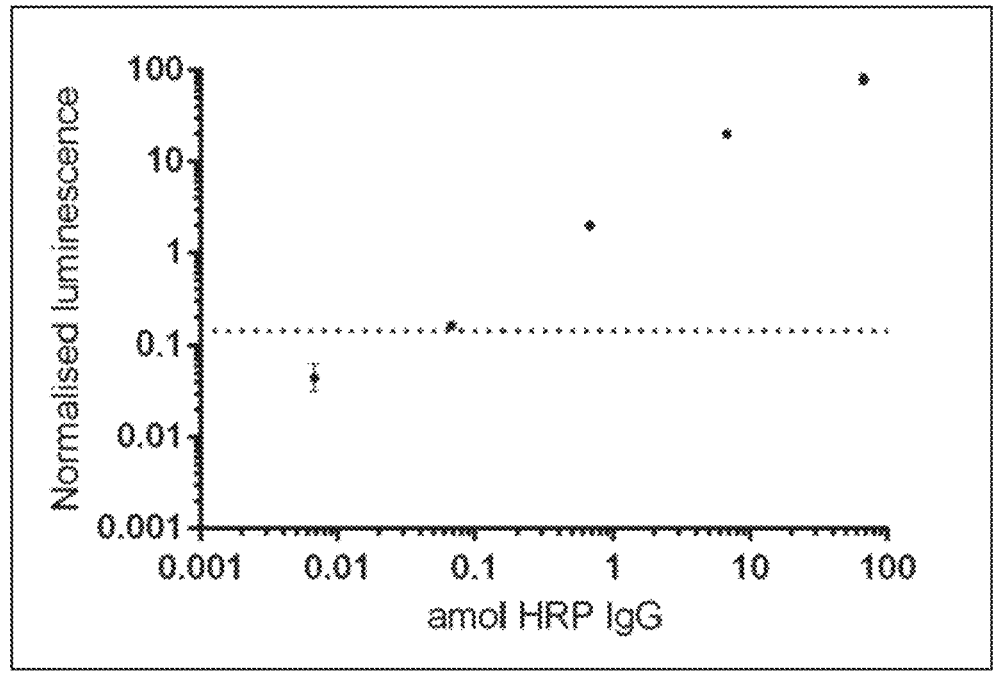
FIG. 4A: The normalized luminescence measured on the assembly comprising the flow cell according to the invention and an optical CMOS sensor (Average of n=3) for different concentration of HRP-IgG. The error bar shows the SD of the triplicate measurements and the dotted line shows the threshold value, defined by "The average of the blank+3×SD" (n=3).
FIG. 4B: Table showing the performance of readout in the assembly comprising the flow cell according to the invention and an optical CMOS sensor compared with lab based immunoassays.

The results (see FIG. 4A) show that the lowest concentration of HRP-IgG that was still detectable with the assembly comprising the flow cell according to the present invention and an optical CMOS sensor is 0.0676 amol HRP-IgG (conjugate) (or 676 aM). This shows that the assembly allows the readout of immunoassays with a higher sensitivity than classical lab based immunoassays (see FIG. 4B).

Example 3

Amyloid β42 (Aβ42) Detection with a Chemiluminescent Bead ELISA

To demonstrate that the assembly comprising the flow cell according to the present invention and an optical CMOS sensor can be used for the readout of biological assays, the performance of a peptide assay, more specific Aβ42 assay, was tested.

In this assay, a serial dilution of synthetic Aβ42 peptide (Anaspec, USA) was measured. For this assay, 5 mg of Dynabeads M-270 Epoxy (Life technologies, Gent, Belgium) were coated with 50 µg of Aβ42 specific antibodies which bind with the c-terminal end of Aβ42 (JRF/cAβ42/26) (Department of Neuroscience at Janssen R & D, Belgium) according to the manufacturer's instructions of the Dynabeads antibody coupling kit (Life technologies, Gent, Belgium). The coated beads were blocked with casein just before use, by incubation in 1% casein PBS Buffer (Thermoscientific, Leuven, Belgium) on a roller at room temperature for 5 min (1 µl of 10 mg beads/ml in 99 µl blocking solution per sample). A serial dilution of Aβ42 was prepared in 0.1% casein. The Aβ42 dilutions were premixed with an amyloid specific detection antibody conjugated with HRP which binds to the a-terminal end amyloid (JRF/AβN/25-HRP) (Department of Neuroscience at Janssen R & D, Belgium). After the blocking step, the beads were separated from the blocking solution with the use of an external magnet and 100 µl of the Aβ42-detection antibody mixture was added to the beads and incubated for 30 min on a roller at room temperature. After this incubation, non-bound antibodies were washed away in three wash steps with 200 µl PBST (PBS+0.05% Tween) and one with 50 µl PBS. For each wash step, beads were separated from the liquid with the use of an external magnet and were dissolved in wash buffer. After the last wash step the detection was performed following the protocol as described in Example 1.

Figures 5A, 5B:
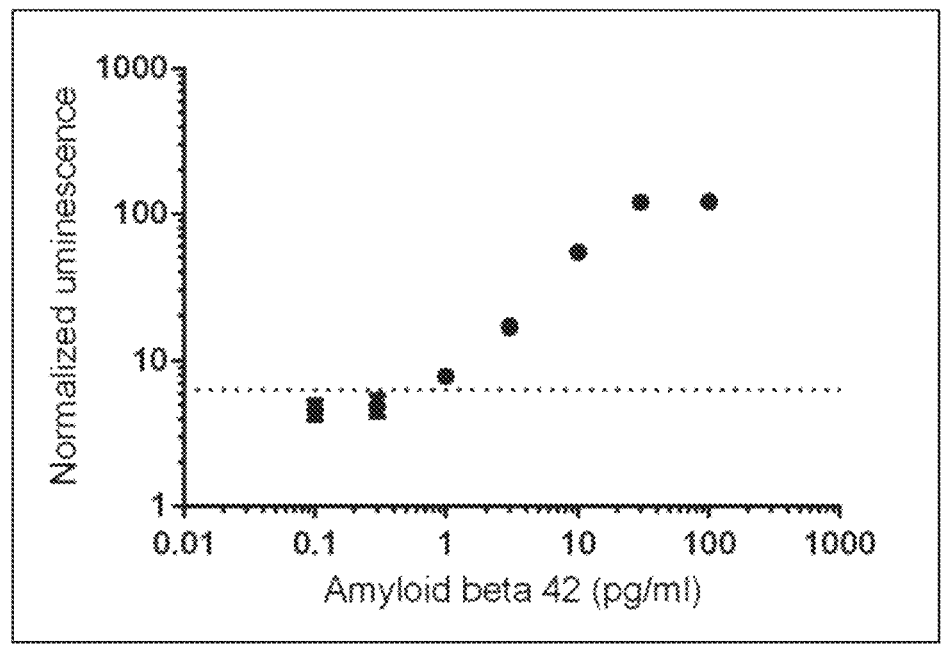
FIG. 5A: Detection of amyloid beta 42 by a chemiluminescent bead ELISA with readout in the assembly comprising the flow cell according to the invention and an optical CMOS sensor. The error bar shows the SD of the triplicate measurements and the dotted line shows the threshold value, defined by "The average of the blank+3×SD" (n=3).
FIG. 5B: Table showing the performance of chemiluminescent bead ELISA with readout in the assembly comprising the flow cell according to the invention and an optical CMOS sensor compared with commercial available Aβ 42 lab-based assays, according to LLOD reported by manufacturers.

FIG. 5A shows the results of the detection of different concentrations of Aβ42 with a chemiluminescent bead ELISA with readout in the assembly comprising the flow cell according to the present invention and an optical CMOS sensor. The detection of amyloid beta 42 with assembly shows a LLOD of 1 pg/ml or 200 fM, which is more sensitive than the commercial available colorimetric plate ELISAs for amyloid beta 42 detection (see FIG. 5B).

Example 4

IFN-Gamma-Inducible Protein 10 (IP-10) Detection with a Chemiluminescent Bead ELISA To demonstrate the readout of a protein detection assay, the performance of IP-10 detection with a chemiluminescent bead ELISA with readout in the assembly comprising the flow cell according to the present invention and an optical CMOS sensor was tested.

In this assay, a serial dilution of recombinant human IP-10 (Life technologies, Gent, Belgium) was measured. For this assay, 5 mg of Dynabeads M-270 Epoxy (Life technologies, Gent, Belgium) were coated with 50 µg of human IP-10 specific capture antibodies from the IP-10 Human Antibody Pair kit (Life technologies, Gent, Belgium) according to the manufacturer's instructions of the Dynabeads antibody coupling kit (Life technologies, Gent, Belgium). The coated beads were blocked with casein just before use, by incubation in 1% casein PBS Buffer (Thermoscientific, Leuven, Belgium) on a roller at room temperature for 5 min (1 µl of 10 mg beads/ml in 99 µl blocking solution per sample). A serial dilution of human IP-10 was prepared in 1% casein PBS Buffer (Thermoscientific, Leuven, Belgium). After the blocking step, the blocking solution was replaced by the diluted human IP-10 and incubated for 1 h at room temperature. After this incubation, non-bound antibodies were washed away in three wash steps with 200 µl PBST (PBS+0.05% Tween) and one with 100 µl PBS. After the wash steps, the bound IP-10 were detected with the biotin conjugated detection antibody from the IP-10 Human Antibody Pair kit (Life technologies, Gent, Belgium). Therefore, 100 µl of 0.2 µg/ml detection antibody (1000 times diluted in 1% casein PBS Buffer (Thermoscientific, Leuven, Belgium)) was added to each well and incubated for 1 h at room temperature. After this incubation step, non-bound antibodies were washed away in three wash steps with 200 µl PBST (PBS+0.05% Tween) and one with 100 µl PBS. The last incubation step was performed with 100 µl HRP conjugated streptavidin from the IP-10 Human Antibody Pair kit (Life technologies, Gent, Belgium) (600 times diluted in 1% casein PBS Buffer (Thermoscientific, Leuven, Belgium)) for 1 h at room temperature. After this last incubation step, non-bound antibodies were washed away in three wash steps with 200 µl PBST (PBS+0.05% Tween) and one with 50 µl PBS. Afterwards, the detection was performed following the protocol as described in Example 1.

A concentration gradient of IP-10 was measured in triplicate (see FIG. 6A). The detection of IP-10 with the assembly comprising the flow cell according to the invention and an optical CMOS sensor shows a LLOD of 4 pg/ml or 460 fM, which is in the same range as commercial available colorimetric plate ELISAs and Fluorescent bead based ELISAs (see FIG. 6B).

Example 5

Antibodies Specific for Polyomavirus Capsid Protein 1 (JCV VP1) Detection with a Chemiluminescent Bead ELISA In addition to the readout of antigen (peptide/protein) assays also the readout of antibody assays can be performed with the assembly comprising the flow cell according to the present invention and an optical CMOS sensor.

In this assay, antibodies for JCV VP1 were measured in a serial dilution of a positive plasma sample. For this assay, 5 mg of Dynabeads M-270 Epoxy (Life technologies, Gent, Belgium) were coated with 50 µg of recombinant JCV VP1 (Abcam, Cambridge, UK) according to the manufacturer's instructions of the Dynabeads antibody coupling kit (Life technologies, Gent, Belgium). The coated beads were blocked with casein just before use, by incubation in 1% casein PBS Buffer (Thermoscientific, Leuven, Belgium) on a roller at room temperature for 5 min (1 µl of 10 mg beads/ml in 99 µl blocking solution per sample). A serial dilution of a positive plasma sample was prepared in 1% casein PBS Buffer (Thermoscientific, Leuven, Belgium). After the blocking step, the beads were separated from the blocking solution with the use of an external magnet and 100 µl of the diluted plasma was added to the beads and incubated for 1 h on a roller at room temperature. After this incubation, non-bound antibodies were washed away in three wash steps with 200 µl PBST (PBS+0.05% Tween) and one with 50 µl PBS. For each wash step, beads were separated from the liquid with the use of an external magnet and were dissolved in wash buffer. To detect the amount of anti-VP1 antibodies bound, an anti-human IgG conjugated with HRP (HRP-IgG) (Ortho Clinical Diagnostics, USA) was used as detection antibody. This detection antibody was 10000 times diluted in 1% casein PBS Buffer (Thermoscientific, Leuven, Belgium). 100 µl of this diluted detection antibody was incubated with the beads for 30 min on a roller at room temperature. After this last incubation step, non-bound antibodies were washed away in three wash steps with 200 μl PBST (PBS+0.05% Tween) and one with 50 μl PBS. Afterwards, the detection was performed following the protocol as described in Example 1.

As a comparison, the amount of JCV VP1 specific antibodies in the same positive plasma sample was determined with a colorimetric plate ELISA as described below.

Antibodies Specific for Polyomavirus Capsid Protein 1 (JCV VP1) Detection with a Colorimetric Plate ELISA In this colorimetric plate ELISA, antibodies for JCV VP1 were measured in a serial dilution of the same positive plasma sample used for the chemiluminescent bead ELISA with readout with the assembly comprising the flow cell of the present invention and an optical CMOS sensor. Therefore, the wells of a transparent 96 well maxisorp plate were coated with recombinant JCV VP1 (Abcam, Cambridge, UK) by an overnight incubation at room temperature with 100 μl of 1 μg/ml recombinant JCV VP1 dissolved in PBS. After the overnight incubation, the wells were washed with 200 μl PBST (PBS+0.05% Tween) and blocked by a one hour incubation at room temperature with 200 μl PBS+1% BSA. A serial dilution of a positive plasma sample was prepared in 1% casein PBS Buffer (Thermoscientific, Leuven, Belgium). After the blocking step, the blocking solution was replaced by the diluted plasma sample and incubated for 1 h at room temperature. After this incubation, non-bound antibodies were washed away in three wash steps with 200 μl PBST (PBS+0.05% Tween) and the bound antibodies were detected with an anti-human IgG conjugated with HRP (HRP-IgG) (Ortho Clinical Diagnostics, USA). Therefore, 100 μl of detection antibody (1000 times diluted in 1% casein PBS Buffer (Thermoscientific, Leuven, Belgium)) was added to each well and incubated 30 min at room temperature. After this last incubation step, non-bound antibodies were washed away in four wash steps with 200 μl PBST (PBS+0.05% Tween). Finally, the amount of HRP-IgG bound was visualized by incubation with 100 μl TMB substrate per well during 10 min at room temperature. After this 10 min incubation, the reaction was stopped by adding an equal volume of 1N HCl per well. The optical density was than measured at 450 nm with the SPECTRAmax 384 Plus (Molecular devices, California, United States).

Figure 7A:
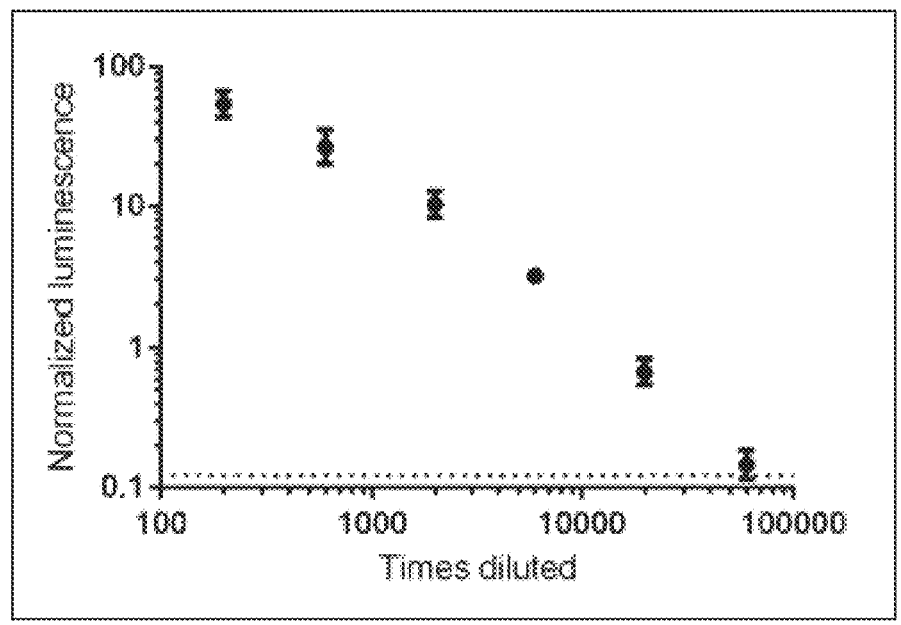
FIG. 7A: Detection of anti VP1 antibodies in a diluted positive plasma sample by a chemiluminescent bead ELISA with readout in the assembly comprising the flow cell according to the invention and an optical CMOS sensor.
Figure 7B:
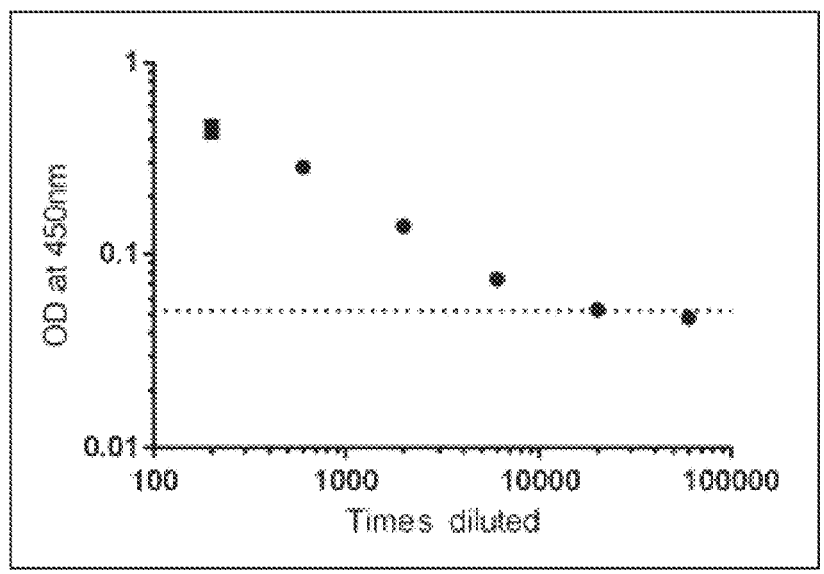
FIG. 7B: Detection of anti VP1 antibodies in a diluted positive plasma sample by a colorimetric plate ELISA. The error bars show the SD of the triplicate measurements and the dotted line shows the threshold value, defined by "The average of the blank+3×SD" (n=3).

The results in FIGS. 7A and 7B show that the sensitivity of the chemiluminescent bead ELISA with readout in the developed assembly comprising the flow cell according to the present invention and an optical CMOS sensor is 7-fold more sensitive as the colorimetric plate-based ELISA. The lowest detectable dilution with the chemiluminescent bead ELISA with readout in the developed assembly was 82458 times diluted, compared with 12428 times diluted for the colorimetric plate ELISA.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A channel for trapping particles to be fed to said channel with a fluid, said channel having a bottom and opposite sidewalls and defining a first longitudinal direction, the sidewalls defining a width of the channel, said channel further comprising:
   a first channel part;
   a second channel part in fluid through flow connection with said first channel part and located in the first longitudinal direction with respect to said first channel part;
   an elevated structure provided in said channel that divides said channel into said first channel part and said second channel part and for trapping particles in said first channel part;
   at least one flow gap provided by said elevated structure for providing said fluid through flow connection between the first channel part and the second channel part for allowing, in use, at least some fluid to flow past said elevated structure into said second channel part while trapping said particles in said first channel part;
   wherein said elevated structure is substantially U-shaped having a base extending substantially between the opposite sidewalls of the channel, thereby covering substantially the entire width of the channel, and two legs extending from the base in a second longitudinal direction, opposite the first longitudinal direction, wherein at least part of said U-shaped elevated structure defines at least part of a particle trapping area for trapping the particles to be fed to said channel.

2. The channel according to claim 1, wherein at least a part of said elevated structure has a height that is smaller than at least a local height of said channel in the area of the elevated structure, thereby providing said at least one flow gap.

3. The channel according to claim 1, wherein said legs have a substantially uniform width over the lengths thereof.

4. The channel according to claim 1, wherein said legs have a substantially tapering width in the first longitudinal direction.

5. The channel according to claim 1, wherein said legs have a length that is between 0.5 to 1 times the length of the particle trapping area.

6. The channel according to claim 1, wherein said second channel part is at least locally wider than said first channel part in the area of the elevated structure.

7. The channel according to claim 1, wherein the width of the channel is 25 or more times its height.

8. The channel according to claim 1, wherein said channel is a microfluidic channel.

9. The channel according to claim 1, wherein said channel has capillary action.

10. A flow cell, said flow cell comprising:
 a channel according to claim 1, and
 an inlet port and an outlet port that are in fluid through flow connection with said channel.

11. An assembly of a flow cell according to claim 10 and a detector.

12. A method for trapping particles in a channel, said method comprising the steps of:
 (a) providing a said channel according to claim 1;
 (b) feeding a fluid with particles to be trapped to said first channel part for trapping said particles in said particle trapping area.

13. The method according to claim 12, wherein said particles are coated with target molecules or capture molecules.

14. The method according to claim 12, wherein the particles fed to said first channel part in step (b) have a minimum cross sectional size that is larger than said at least one flow gap.

15. A method for analyzing a sample, said method comprising the steps of:
 (a) providing an assembly according to claim 11;
 (b) feeding a fluid with particles to be trapped to said first channel part for trapping said particles in said particle trapping area, said particles being coated with capture molecules for capturing target molecules from said sample to be analyzed;
 (c) feeding said sample to be analyzed to said first channel part, and
 (d) feeding detection antibody conjugated with an enzyme to said first channel part, and
 (e) analyzing said sample by means of said detector.

16. A method for analyzing a sample, said method comprising the steps of:
 (a) providing an assembly according to claim 11;
 (b) feeding a fluid with particles to be trapped to said first channel part for trapping said particles in said particle trapping area, said particles being coated with target molecules of a sample to be analyzed;
 (c) feeding detection antibody conjugated with an enzyme to said first channel part, and
 (d) analyzing said sample by means of said detector.

17. A channel according to claim 2, wherein said second channel part is at least locally wider than said first channel part in the area of the elevated structure.

18. A channel according to claim 2, wherein said channel has a width that is 25 or more times its height.

19. A channel according to claim 2, wherein said channel is a microfluidic channel.

20. A channel according to claim 6, wherein said channel has a width that is 25 or more times its height.

* * * * *